United States Patent [19]

Handrick et al.

[11] 4,185,024

[45] Jan. 22, 1980

[54] NITRIC ACID PROCESS FOR THE MANUFACTURE OF ANTHRAQUINONE FROM O-BENZYL-TOLUENE

[75] Inventors: Kurt Handrick, Essen-Steele; Georg Kölling, Essen-Bredeney; Clemens Linden, Essen-Bergerhausen, all of Fed. Rep. of Germany

[73] Assignee: Bergwerksverband GmbH, Essen, Fed. Rep. of Germany

[21] Appl. No.: 8,388

[22] Filed: Feb. 1, 1979

[30] Foreign Application Priority Data

Feb. 2, 1978 [DE] Fed. Rep. of Germany ....... 2804417

[51] Int. Cl.² .................... C07C 49/68; C09B 1/00
[52] U.S. Cl. ................................................ 260/369
[58] Field of Search ........................................ 260/369

[56] References Cited
U.S. PATENT DOCUMENTS 4,036,861   7/1977   Togo et al. .................... 260/369

OTHER PUBLICATIONS

*Chemical Abstract,* vol. 87, No. 93096w, 1975, Tsutomo et al., "o-Benzoyl-benzoic acid and anthraquinone".

*Primary Examiner*—Patrick Garvin
*Assistant Examiner*—Raymond K. Covington
*Attorney, Agent, or Firm*—Michael J. Striker

[57] ABSTRACT

A process for the manufacture of anthraquinones in which o-benzyl-toluene is first oxidized with 25 to 50 weight-% nitric acid at atmospheric pressure and moderate temperatures, and then further oxidized with a more dilute nitric acid at elevated temperatures and pressures to yield crude o-benzoyl-benzoic acid. The crude product is then esterified with methanol, the methyl ester distilled and, when necessary, recrystallized, and heated with concentrated sulfuric acid to yield anthraquinone in high yield and of a high degree of purity.

5 Claims, No Drawings

NITRIC ACID PROCESS FOR THE MANUFACTURE OF ANTHRAQUINONE FROM O-BENZYL-TOLUENE

BACKGROUND OF THE INVENTION

The invention concerns a process for the production of anthraquinone through the oxidation of o-benzyl-toluene with nitric acid under pressure at elevated temperatures.

Anthraquinone is a starting material in the manufacture of valuable dyes which are required by the textile industry in ever-increasing amounts.

A known process involves the oxidation of mixtures of o- and p-benzyl-toluene with dilute nitric acid under pressure at temperatures of 135°–200° C. The reaction mixture is treated with concentrated sulfuric acid to effect the conversion of the o-benzolyl-benzoic acid to anthraquinone; the residual p-benzoyl-benzoic acid is extracted with a soda solution (Acta Chem. Scand. 9, 177–178, 1955; Chem. Abstr. 1956, 4080i). There is no discussion of the purity of the product, in particular with reference to the considerable quantities of nitration by-products. Repetition of the known process lead to the discovery that o-benzyl toluene is unusually susceptible to nitration during the oxidation process with nitric acid. If the oxidation is carried out in the known manner with nitric acid under pressure, only a small amount of the desired o-benzyl-benzoic acid is produced; the reaction product consists primarily of nitration products, in particular nitro-o-benzoyl benzoic acids. For this reason, it is not possible to obtain a pure anthraquinone in good yield with this procedure. If the resultant raw product is treated with sulfuric acid at elevated temperatures, the solution becomes black from the dissociation of the nitro compounds.

DESCRIPTION OF THE INVENTION

It is therefore a goal of the invention to suppress the nitration reactions which occur during the oxidation of o-benzyl-toluene with nitric acid and to obtain pure anthraquinone in high yield through the cyclization of the o-benzoyl-benzoic acid with concentrated sulfuric acid.

According to the method of the present invention, the oxidation is first carried out with 25 to 50 weight-% nitric acid in the presence of known oxidation catalysts at atmospheric pressure and at temperatures between 80°–110° C. until the evolution of nitrogen oxides has abated. The liquid oxidation product is then treated with 8 to 15 weight-% nitric acid under pressures of from 10 to 30 bar and temperatures of from 150°–180° C. until the nitrogen oxide evolution ceases. The crude o-benzoyl-benzoic acid is esterified by conventional procedures with methanol, the methyl ester distilled off and if required recrystallized, and finally converted to anthraquinone through heating with concentrated sulfuric acid at a temperature of around 150° C.

In the first oxidation step the weight ratio of o-benzyl toluene to half-concentrated nitric acid, according to the variation in concentration of the nitric acid from 25 to 50%, should approximate 1:6 to 1:10. As there are two phases, it is required that the reaction be carried out in agitation vessels, or if a continuous process is desired, in a cascade of agitation vessels. It is further advantageous to add to the sulfuric acid known oxidation catalysts; for example, oxides and salts of vanadium, molybdenum, cobalt or manganese have been employed. The termination of the first oxidation step is indicated by the abatement of nitrogen oxide evolution, which occurs after about 4–6 hours. Through the use of a neutralized or deacidified probe it can be determined, for example by gas chromatography, if all of the benzyl-toluene has reacted.

The product of the first oxidation step is predominantly o-benzoyl-toluene; however, the reaction mixture already contains a small amount of o-benzoyl-benzoic acid as well as nitro-products, the latter mainly in the form of nitric acid esters.

The nitric acid phase is then separated from the hydrocarbon phase, and the latter then subjected to the pressure oxidation with nitric acid. The recovered nitric acid phase can be used repeatedly upon reconcentration with fresh nitric acid. The pressure oxidation is carried out at temperatures between 155°–165° C. with diluted nitric acid of between 8 and 15 weight-% at a weight ratio of about 1:15 to 1:20 with respect to the crude o-benzoyl-toluene. The pressure is allowed to rise to between 10–30 bar, any excess pressure being occasionally released. When large quantities are treated, it is advantageous to perform the oxidation in an autoclave, wherein is the nitric acid heated to the temperature of the reaction and the crude o-benzoyl-toluene is gradually pumped in. The pressure oxidation is completed after 1–2 hours. After cooling of the oxidation product the crude-o-benzoyl-benzoic acid falls out of solution. The product is filtered out and dried; the nitric acid mother liquor is recycled after reconcentration.

The total dissociation of the nitric acid in both steps is about 950 g per kilogram of o-benzoyl-benzoic acid produced. As almost half of the gas evolved consists of nitrogen oxides (NO and $NO_2$) which can be regenerated to nitric acid, the effective amount of nitric acid used is about 500 g per kilogram of o-benzoyl-benzoic acid. The costly discharge through the oxidation material is thus very small.

The raw o-benzoyl-benzoic acid contains about 0.3–0.5% nitrogen. The raw acid is therefore next esterified with methanol and the methyl ester separated from the accompanying by-products through distillation. The esterification may be effected through the conventional method in the presence of acid catalysts, such as hydrochloric, sulfuric or p-toluenesulfonic acids, or alternatively without addition of catalysts under pressure at temperatures above 200° C. The pure o-benzoyl-benzoic acid methyl ester distills at a pressure of 8 Torr over the range 177°–181° C. It solidifies to colorless crystals with a melting point of 52.5° C. The nitrated products remain in the sump of the distillation apparatus.

It is possible that the ester might retain a slight color after distillation and have a nitrogen content of at most 0.1%. In this case, the ester may be recrystallized; the solvent of choice is isopropyl alcohol. The ester falls out of such solution in a granular crystalline form.

The o-benzoyl-benzoic acid methyl ester is then mixed with the known materials for effecting the cyclization of o-benzoyl-benzoic acid without any saponification of the ester. It is surprising that the methyl ester may be converted quantitatively to anthraquinone upon heating to about 150° C. with concentrated sulfuric acid, the technically preferred method for cyclization of o-benzoyl-benzoic acid. It is known that strong mineral acids can saponify esters; however, such saponifications are not generally uniform and complete.

The above procedure is not limited to the manufacture of anthraquinone. In a similar manner, substituted anthraquinones may be prepared; for example, one may use chloro-, nitro- or alkyl-substituted o-benzyl-toluenes as starting materials to obtain the corresponding substituted products.

The invention may be better understood through the following examples.

EXAMPLE 1

In a reaction vessel provided with a stirred and reflux condenser a mixture of 910 g o-benzyl-toluene (5 Mol), 4.5 l of 40 weight-% nitric acid (density 1.24) and 4 g of freshly precipitated vanadium pentoxide is heated to 95° C. under stirring. After about 5½ hours the evolution of nitrogen oxides ceases. After cooling the liquid raw o-benzoyl-toluene is separated from the nitric acid phase. It is pumped during about 30 minutes into a 20 l autoclave of V2A steel, provided with stirrers, vents, a manometer and filling caps, in which are 15 l of 12 weight-% nitric acid (density 1.065) heated to 160° C. The pressure, which increased on account of the nitrogen oxides evolved, is maintained at about 20 bar. Finally, the temperature is raised to about 170° C. while the pressure is held constant. After about 1 hour oxidation is completed. The contents of the autoclave is cooled and the precipitated crude o-benzoyl-benzoic acid is isolated. The yield approaches 1080 g, the acid number 238 (theory=248) and the nitrogen content 0.42%.

The isolated crude product is then esterified with 2.2 l methanol and a catalytic amount of concentrated sulfuric acid for 4 hours at 70° C. About 13.5 g of insoluble material is filtered from the solution. After distillation of the excess methanol the ester is worked up in the customary manner. 24.3 g of unesterified o-benzoyl-benzoic acid 995 g of o-benzoyl-benzoic acid methyl ester is thus recovered and 1107 g of the crude ester are distilled using a column under a pressure of 5 Torr over the range 171°–174° C. The yield is 1020 g with a nitrogen content of 0.08%; the product is a light yellow.

The product is dissolved in 2.5 l of warm isopropyl alcohol. After 6 hours the ester precipitates in a granular crystalline form. 825 g of colorless ester with a melting point of 52° C. and a nitrogen content of less than 0.03% is recovered. The filtrate is concentrated, the crude ester distilled off and the distillate recrystallized. In this manner a further 170 g of the purified ester is recovered, making the total yield 995 g. dissolved with warming in 3.5 l concentrated sulfuric acid and mixture heated for 1 hour to 150° C. After the conventional work-up 863 g of pure anthraquinone with a melting point of 286° C. is obtained.

With the addition of the product derived from the o-benzoyl-benzoic acid which was not esterified, the yield of anthraquinone, calculated from the starting o-benzyl-toluene, is about 85% of theory.

COMPARISON EXAMPLE 2a

In a 2 l autoclave of V2A steel 91 g (0.5 Mol) o-benzyl-toluene and 750 ml 15% nitric acid (density 1.08) are heated. An exothermic reaction begins at about 140° C. which causes the temperature to rise to about 180° C. The pressure is held constant at about 30 bar. After termination of the reaction the mixture is cooled and an additional 750 ml of 15% nitric acid added. The reaction is carried out to completion at about 200° C. and 30 bar pressure. 104 g of a brown product is recovered with a nitrogen content of 3.9%; it is comprised substantially of nitro-o-benzoyl-benzoic acids. The product turns black upon heating with concentrated sulfuric acid.

COMPARISON EXAMPLE 2b

A 2 l stirring autoclave is filled with 60.7 g (⅓ Mol) o-benzyl-toluene and 1.2 l 12 weight-% nitric acid (density 1.065) and slowly heated up. The oxidation begins at about 155° C.; the temperature is gradually raised to 170° C. and kept constant for about an hour. The pressure is held at about 20 bar. After cooling the precipitated product is filtered off and dried. The yield approaches 67.5 g, the acid number 177 and the nitrogen content 4.2%. The product turns black upon heating with concentrated sulfuric acid.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process for the production of anthraquinone, comprising oxidizing o-benzyl-toluene with 25 to 50 weight-% nitric acid in the presence of known oxidation catalysts at atmospheric pressure and a temperature between about 80° and 110° C. until evolution of nitrogen oxides ceases; further oxidizing the product of said first oxidation step with 8 to 15 weight-% nitric acid under a pressure of between about 10 to 30 bar and a temperature between about 150° and 180° C. until evolution of nitrogen oxides ceases, to yield crude o-benzoyl-benzoic acid; esterifying said crude o-benzoyl-benzoic acid with methanol, to yield a corresponding methyl ester; distilling said methyl ester from the reaction mixture; and heating said methyl ester with concentrated sulfuric acid at a temperature of about 150° to yield anthraquinone.

2. A process as defined in claim 1, further comprising a recrystallization of the methyl ester from isopropyl alcohol.

3. A process as defined in claim 1, wherein said oxidation catalysts are oxides or salts of vanadium, molybdenum, cobalt or manganese.

4. A process as defined in claim 1, wherein in the first oxidation step the weight ratio of o-benzyl-toluene to nitric acid is between about 1:6 to 1:10.

5. A process as defined in claim 1, wherein in the second oxidation step the weight ratio of o-benzoyl-toluene to diluted nitric acid is between about 1:15 to 1:20.

* * * * *